United States Patent
Denti et al.

(10) Patent No.: US 10,441,266 B2
(45) Date of Patent: Oct. 15, 2019

(54) POST-IMPLANTATION TENSION ADJUSTMENT IN CARDIAC IMPLANTS

(71) Applicant: 4Tech Inc., Waltham, MA (US)

(72) Inventors: Paolo Denti, Milan (IT); Andrea Guidotti, Zurich (CH); Kevin Lynn, Athenry (IE); Idan Tobis, Beth Hashmonai (IL)

(73) Assignee: 4Tech Inc., Waltham, MA (US)

( * ) Notice: Subject to any disclaimer, the term of this patent is extended or adjusted under 35 U.S.C. 154(b) by 0 days.

(21) Appl. No.: 15/903,619

(22) Filed: Feb. 23, 2018

(65) Prior Publication Data

US 2018/0249993 A1 Sep. 6, 2018

Related U.S. Application Data

(60) Provisional application No. 62/465,400, filed on Mar. 1, 2017.

(51) Int. Cl.
*A61F 2/24* (2006.01)
*A61B 17/04* (2006.01)
(Continued)

(52) U.S. Cl.
CPC ........ *A61B 17/0401* (2013.01); *A61F 2/2442* (2013.01); *A61F 2/2445* (2013.01);
(Continued)

(58) Field of Classification Search
CPC ........ A61F 2/24; A61F 2/2454; A61F 2/2457; A61F 2/848; A61F 2/8483;
(Continued)

(56) References Cited

U.S. PATENT DOCUMENTS

| 4,602,911 A | 7/1986 | Ahmadi et al. |
| 5,474,518 A | 12/1995 | Farrer Velazquez |

(Continued)

FOREIGN PATENT DOCUMENTS

| WO | 2006097931 A2 | 9/2006 |
| WO | 2006111391 A1 | 10/2006 |

(Continued)

OTHER PUBLICATIONS

JPO, Office Action dated Mar. 27, 2018, Japanese Patent Application No. 098926/2017 (English translation).

(Continued)

*Primary Examiner* — Seema Mathew
(74) *Attorney, Agent, or Firm* — UltimatEdge IP Law Group, P.C.; Dean G. Stathakis; Vito A. Canuso, III (57) ABSTRACT

A method of treating a heart of a patient is provided, including implanting a first tissue anchor in cardiac tissue of the patient, the first tissue anchor attached to one or more tethers that are fixed to a coupling element. A second tissue anchor is implanted in the patient. The coupling element is coupled to a first coupling site of the second tissue anchor, thereby coupling the first tissue anchor to the second tissue anchor via the one or more tethers. Thereafter, after allowing at least 24 hours for tissue growth on the first tissue anchor to strengthen anchoring of the first tissue anchor in the cardiac tissue, tension is increased between the first and the second tissue anchors by decoupling the coupling element from the first coupling site and coupling the coupling element to a second coupling site of the second tissue anchor. Other embodiments are also described.

23 Claims, 6 Drawing Sheets

(51) Int. Cl.
*A61F 2/848* (2013.01)
*A61F 2/915* (2013.01)
*A61B 17/00* (2006.01)

(52) U.S. Cl.
CPC ............ *A61F 2/2454* (2013.01); *A61F 2/848* (2013.01); *A61F 2/915* (2013.01); *A61B 2017/00783* (2013.01); *A61B 2017/0409* (2013.01); *A61B 2017/0412* (2013.01); *A61B 2017/0462* (2013.01); *A61B 2017/0464* (2013.01); *A61B 2017/0496* (2013.01)

(58) Field of Classification Search
CPC ............ A61F 2002/8486; A61F 2/2442; A61F 2/2445; A61B 17/0401; A61B 2017/0412; A61B 2017/0464
See application file for complete search history.

(56) References Cited

U.S. PATENT DOCUMENTS

| | | | |
|---|---|---|---|
| 6,629,534 | B1 | 10/2003 | St. Goar et al. |
| 7,335,213 | B1 | 2/2008 | Hyde et al. |
| 8,029,518 | B2 | 10/2011 | Goldfarb et al. |
| 8,382,829 | B1 | 2/2013 | Call et al. |
| 8,475,525 | B2 | 7/2013 | Maisano et al. |
| 9,241,702 | B2 | 1/2016 | Maisano et al. |
| 9,307,980 | B2 | 4/2016 | Gilmore et al. |
| 9,592,121 | B1 * | 3/2017 | Khairkhahan ........ A61F 2/2463 |
| 10,226,334 | B2 * | 3/2019 | Rowe ................ A61B 17/0401 |
| 2003/0033003 | A1 | 2/2003 | Harrison et al. |
| 2003/0035759 | A1 * | 2/2003 | Coyne .................. B01L 3/5025 422/63 |
| 2003/0105519 | A1 | 6/2003 | Fasol et al. |
| 2004/0186566 | A1 | 9/2004 | Hindrichs et al. |
| 2004/0225304 | A1 | 11/2004 | Vidlund et al. |
| 2004/0243229 | A1 | 12/2004 | Vidlund et al. |
| 2004/0260317 | A1 | 12/2004 | Bloom et al. |
| 2005/0177180 | A1 | 8/2005 | Kaganov |
| 2005/0177224 | A1 | 8/2005 | Fogarty et al. |
| 2006/0058842 | A1 | 3/2006 | Wilke et al. |
| 2006/0241745 | A1 | 10/2006 | Solem |
| 2006/0276890 | A1 * | 12/2006 | Solem .................... A61F 2/2451 623/2.36 |
| 2006/0282161 | A1 | 12/2006 | Huyn et al. |
| 2007/0049942 | A1 | 3/2007 | Hindrichs et al. |
| 2007/0118151 | A1 | 5/2007 | Davidson |
| 2007/0162107 | A1 | 7/2007 | Haug et al. |
| 2007/0270943 | A1 * | 11/2007 | Solem ................ A61B 17/0401 623/2.11 |
| 2007/0282429 | A1 | 12/2007 | Hauser et al. |
| 2008/0027483 | A1 | 1/2008 | Cartledge |
| 2009/0259260 | A1 | 10/2009 | Bentley et al. |
| 2010/0023117 | A1 | 1/2010 | Yoganathan |
| 2010/0161042 | A1 | 6/2010 | Maisano et al. |
| 2010/0217382 | A1 | 8/2010 | Chau et al. |
| 2011/0011917 | A1 | 1/2011 | Loulmet |
| 2011/0029071 | A1 | 2/2011 | Zlotnick et al. |
| 2011/0184510 | A1 * | 7/2011 | Maisano ............ A61B 17/0401 623/1.24 |
| 2012/0035712 | A1 * | 2/2012 | Maisano ............ A61B 17/0401 623/1.26 |
| 2013/0018459 | A1 * | 1/2013 | Maisano ............ A61B 17/0401 623/2.37 |
| 2013/0079873 | A1 * | 3/2013 | Migliazza .......... A61B 17/0401 623/2.17 |
| 2013/0096672 | A1 | 4/2013 | Reich |
| 2013/0325115 | A1 | 12/2013 | Maisano et al. |
| 2014/0114390 | A1 | 4/2014 | Tobis et al. |
| 2014/0324164 | A1 | 10/2014 | Gross et al. |
| 2015/0119936 | A1 | 4/2015 | Gilmore et al. |
| 2015/0223934 | A1 | 8/2015 | Vidlund et al. |
| 2016/0022448 | A1 * | 1/2016 | Tobis ...................... A61F 2/848 623/1.16 |
| 2016/0242762 | A1 | 8/2016 | Gilmore et al. |
| 2016/0346075 | A1 * | 12/2016 | Michalak ................ A61F 2/844 |
| 2018/0221148 | A1 | 8/2018 | Guidotti et al. |
| 2018/0344457 | A1 * | 12/2018 | Gross .................... A61F 2/2418 |

FOREIGN PATENT DOCUMENTS

| | | |
|---|---|---|
| WO | 2011089601 A1 | 7/2011 |
| WO | 2014141239 A1 | 9/2014 |
| WO | 2015006729 A2 | 1/2015 |
| WO | 2015063580 A2 | 5/2015 |
| WO | 2018148324 A1 | 8/2018 |

OTHER PUBLICATIONS

USPTO, Office Action dated Oct. 24, 2017, U.S. Appl. No. 15/365,495.
USPTO, Office Action dated Apr. 12, 2018, U.S. Appl. No. 15/365,495.
USPTO, Office Action dated Jul. 26, 2018, U.S. Appl. No. 15/365,495.
WIPO, Invitation to pay additional fees dated May 4, 2018, International Patent Application Serial No. PCT/US2018/017352.
WIPO, International Search Report and a Written Opinion both dated May 28, 2018, International Patent Application Serial No. PCT/US2018/019420.
WIPO, International Search Report and a Written Opinion both dated Aug. 28, 2018, International Patent Application Serial No. PCT/US2018/017352.
EPO, Extended Search Report dated Dec. 7, 2018, EP Patent Application No. 18183753.5.
USPTO Office Action dated Nov. 25, 2014, U.S. Appl. No. 13/553,081.
WIPO, PCT ISA 210/ISA237 International Search Report and Written Opinion dated Apr. 30, 2019, pp. 10, PCT Patent Application No. PCT/US2018/045523.

* cited by examiner

POST-IMPLANTATION TENSION ADJUSTMENT IN CARDIAC IMPLANTS

CROSS-REFERENCE TO RELATED APPLICATIONS

The present application claims the benefit of U.S. Provisional Application 62/465,400, filed Mar. 1, 2017, which is assigned to the assignee of the present application and is incorporated herein by reference. The present application is related to an international application to Denti et al. filed on even date herewith, entitled, "Post-implantation tension adjustment in cardiac implants."

FIELD OF THE APPLICATION

The present invention relates generally to minimally-invasive valve repair, and more specifically to minimally-invasive methods for repairing the tricuspid valve.

BACKGROUND OF THE APPLICATION

Functional tricuspid regurgitation (FTR) is governed by several pathophysiologic abnormalities such as tricuspid valve annular dilatation, annular shape, pulmonary hypertension, left or right ventricle dysfunction, right ventricle geometry, and leaflet tethering. Treatment options for FTR are primarily surgical.

U.S. Pat. No. 8,475,525 to Maisano et al. describes a method that includes implanting at least a first tissue-engaging element in a first portion of tissue in a vicinity of a heart valve of a patient, implanting at least a second tissue-engaging element in a portion of a blood vessel that is in contact with an atrium of a heart of the patient, and drawing at least a first leaflet of the valve toward at least a second leaflet of the valve by adjusting a distance between the portion of the blood vessel and the first portion of tissue in the vicinity of the heart valve of the patient. In one configuration, a proximal end portion of a longitudinal member is shaped so as to define one or more engaging elements (e.g., hooks or barbs), which are coupleable with the struts of a stent member in order to maintain the tension applied to a longitudinal member for remodeling the tricuspid valve.

SUMMARY OF THE APPLICATION

Some applications of the present invention provide a method of treating a heart of a patient, such as to reduce tricuspid valve regurgitation. The method includes implanting a first tissue anchor in cardiac tissue of the patient, and a second tissue anchor in the patient. The first tissue anchor is attached to one or more tethers that are fixed to a coupling element. The coupling element is coupled to a first coupling site of the second tissue anchor, thereby coupling the first tissue anchor to the second tissue anchor via the one or more tethers. Thereafter, after allowing at least 24 hours for tissue growth on the first tissue anchor to strengthen anchoring of the first tissue anchor in the cardiac tissue, tension is increased between the first and the second tissue anchors by decoupling the coupling element from the first coupling site and coupling the coupling element to a second coupling site of the second tissue anchor.

There is therefore provided, in accordance with an application of the present invention, a method of treating a heart of a patient, including:

implanting a first tissue anchor in cardiac tissue of the patient, the first tissue anchor attached to one or more tethers that are fixed to a coupling element;

implanting a second tissue anchor in the patient;

coupling the coupling element to a first coupling site of the second tissue anchor, thereby coupling the first tissue anchor to the second tissue anchor via the one or more tethers; and thereafter, after allowing at least 24 hours for tissue growth on the first tissue anchor to strengthen anchoring of the first tissue anchor in the cardiac tissue, increasing tension between the first and the second tissue anchors by decoupling the coupling element from the first coupling site and coupling the coupling element to a second coupling site of the second tissue anchor.

For some applications, the one or more tethers are slack before increasing the tension.

For some applications, the coupling element includes a hook.

For some applications, the coupling element is shaped so as to define an opening, and coupling the coupling element to the first coupling site includes coupling the opening to the first coupling site. For some applications, the coupling element includes a loop, which is shaped to define the opening.

For some applications, the second tissue anchor includes a stent that includes a plurality of struts, which define the first and the second coupling sites. For some applications, the first and the second coupling sites extend radially inward to facilitate the coupling of the coupling element to the first and the second coupling sites from within the stent. For some applications, one or more of the struts extend radially inward at the first and the second couplings sites to facilitate the coupling of the coupling element to the first and the second coupling sites from within the stent. For some applications, the second tissue anchor includes hooks at the first and the second coupling sites, respectively.

For some applications, at least one of the struts is oriented axially along the stent, and the axially-oriented strut defines the first and the second coupling sites. For some applications, the first and the second coupling sites extend radially inward to facilitate the coupling of the coupling element to the first and the second coupling sites from within the stent. For some applications, the axially-oriented strut is wider than others of the struts so as to serve as a backbone for the stent.

For some applications, increasing the tension includes increasing the tension after allowing at least one week for tissue growth on the first tissue anchor.

For some applications, increasing the tension includes increasing the tension within two months after implanting the first tissue anchor.

For some applications, the coupling element is a first coupling element, and the one or more tethers are additionally fixed to a second coupling element, and coupling the coupling element to the first coupling site includes coupling one or more of the first and the second coupling elements to a plurality of first coupling sites.

For some applications, coupling the coupling element to the first coupling site includes coupling the coupling element to the first coupling site after implanting the first and the second tissue anchors.

For some applications, coupling the coupling element to the first coupling site includes coupling the coupling element to the first coupling site before implanting the first and the second tissue anchors.

For some applications, coupling the coupling element to the first coupling site includes coupling the coupling element to the first coupling site after implanting the first tissue anchor and before implanting the second tissue anchor.

For some applications, the coupling element is coated with a tissue-growth-inhibiting coating.

For some applications, the first and the second coupling sites are coated with a tissue-growth-inhibiting coating.

For some applications, the first tissue anchor includes a helical tissue-anchoring element.

For some applications, implanting the first tissue anchor includes implanting the first tissue anchor in the vicinity of the tricuspid valve of the patient.

For some applications, implanting the second tissue anchor includes implanting the second tissue anchor in a blood vessel selected from the group consisting of: a superior vena cava (SVC), an inferior vena cava (IVC), and a coronary sinus.

There is further provided, in accordance with an application of the present invention, a system for treating a heart of a patient, including:

a first tissue anchor, which is configured to be implanted in cardiac tissue of the patient;

a coupling element;

one or more tethers, which are attached to the first tissue anchor and are fixed to the coupling element; and a second tissue anchor, which is configured to be implanted in the patient, and which includes a stent that includes a plurality of struts, which define first and second coupling sites to which the coupling element is configured to be coupled so as to couple the first tissue anchor to the second tissue anchor via the one or more tethers, wherein the first and the second coupling sites extend radially inward to facilitate the coupling of the coupling element to the first and the second coupling sites from within the stent, wherein the coupling element is coupleable to the first coupling site, and thereafter decouplable from the first coupling site and couplable to the second coupling site so as to increase tension between the first and the second tissue anchors.

For some applications, the coupling element is shaped so as to define an opening, which is configured to be coupled to the first and the second coupling sites.

For some applications, the coupling element includes a loop, which is shaped to define the opening.

For some applications, the second tissue anchor includes hooks at the first and the second coupling sites, respectively.

For some applications, at least one of the struts is oriented axially along the stent, and the axially-oriented strut defines the first and the second coupling sites. For some applications, the axially-oriented strut is wider than others of the struts so as to serve as a backbone for the stent.

For some applications, one or more of the struts extend radially inward at the first and the second couplings sites to facilitate the coupling of the coupling element to the first and the second coupling sites from within the stent.

For some applications, the coupling element is a first coupling element, and the system includes a second coupling element, which is fixed to the one or more tethers.

For some applications, the coupling element is coated with a tissue-growth-inhibiting coating.

For some applications, the first and the second coupling sites are coated with a tissue-growth-inhibiting coating.

For some applications, the first tissue anchor includes a helical tissue-anchoring element.

The present invention will be more fully understood from the following detailed description of embodiments thereof, taken together with the drawings, in which:

DETAILED DESCRIPTION OF APPLICATIONS

FIGS. 1A-C and 2A-C are schematic illustrations of methods of treating a heart 10 of a patient, in accordance with respective applications of the present invention. For some applications, the methods are performed to treat a tricuspid valve 20, such as by reducing tricuspid valve regurgitation.

Figure 1A:
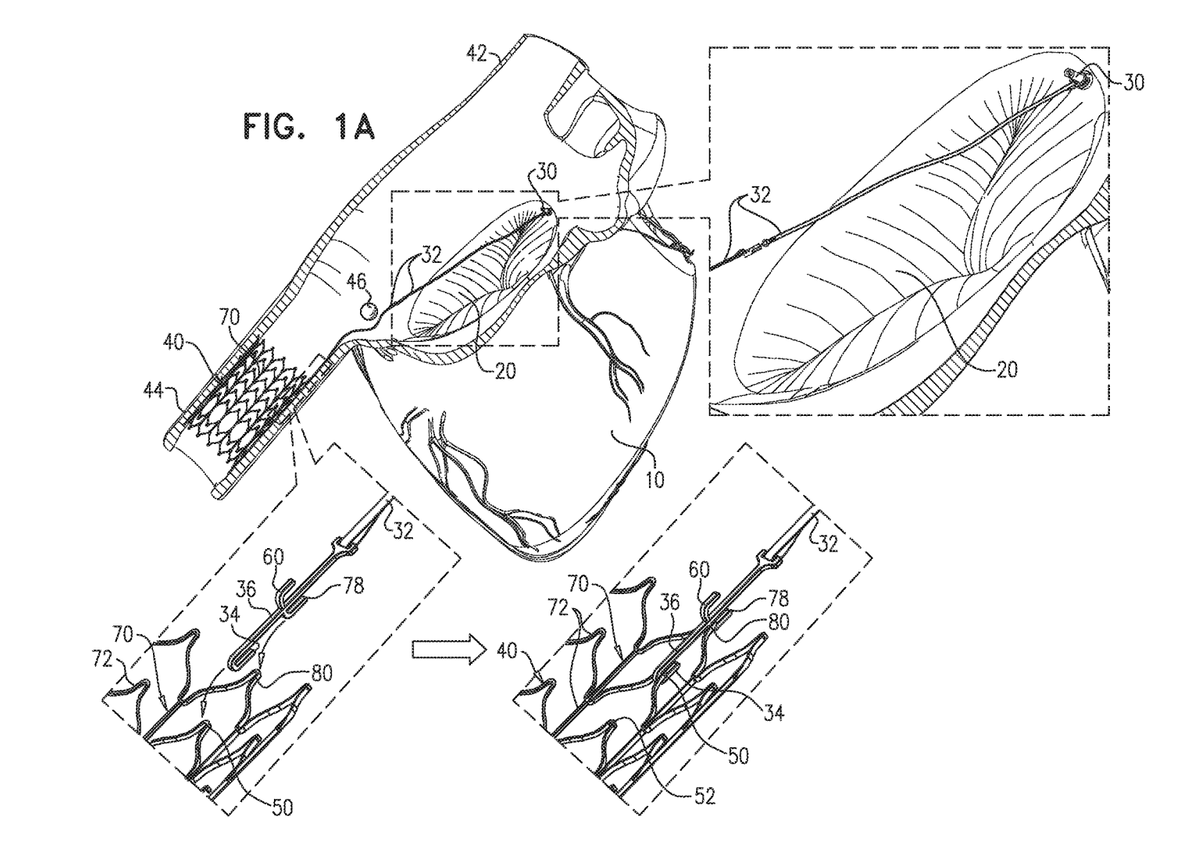
FIGS. 1A-C are schematic illustrations of a method of treating a heart of a patient, in accordance with an application of the present invention.
Figure 1B:
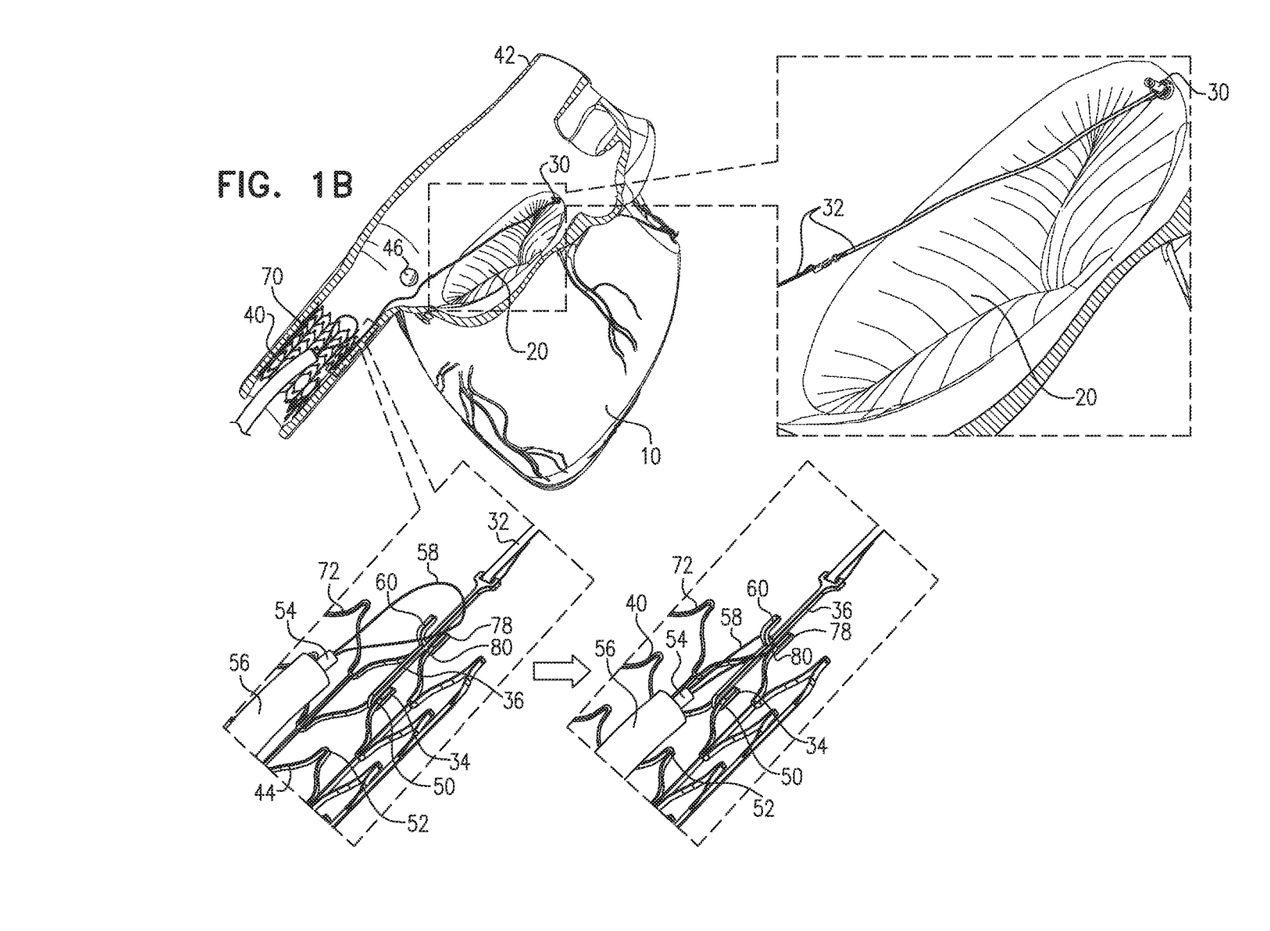
Figure 1C:
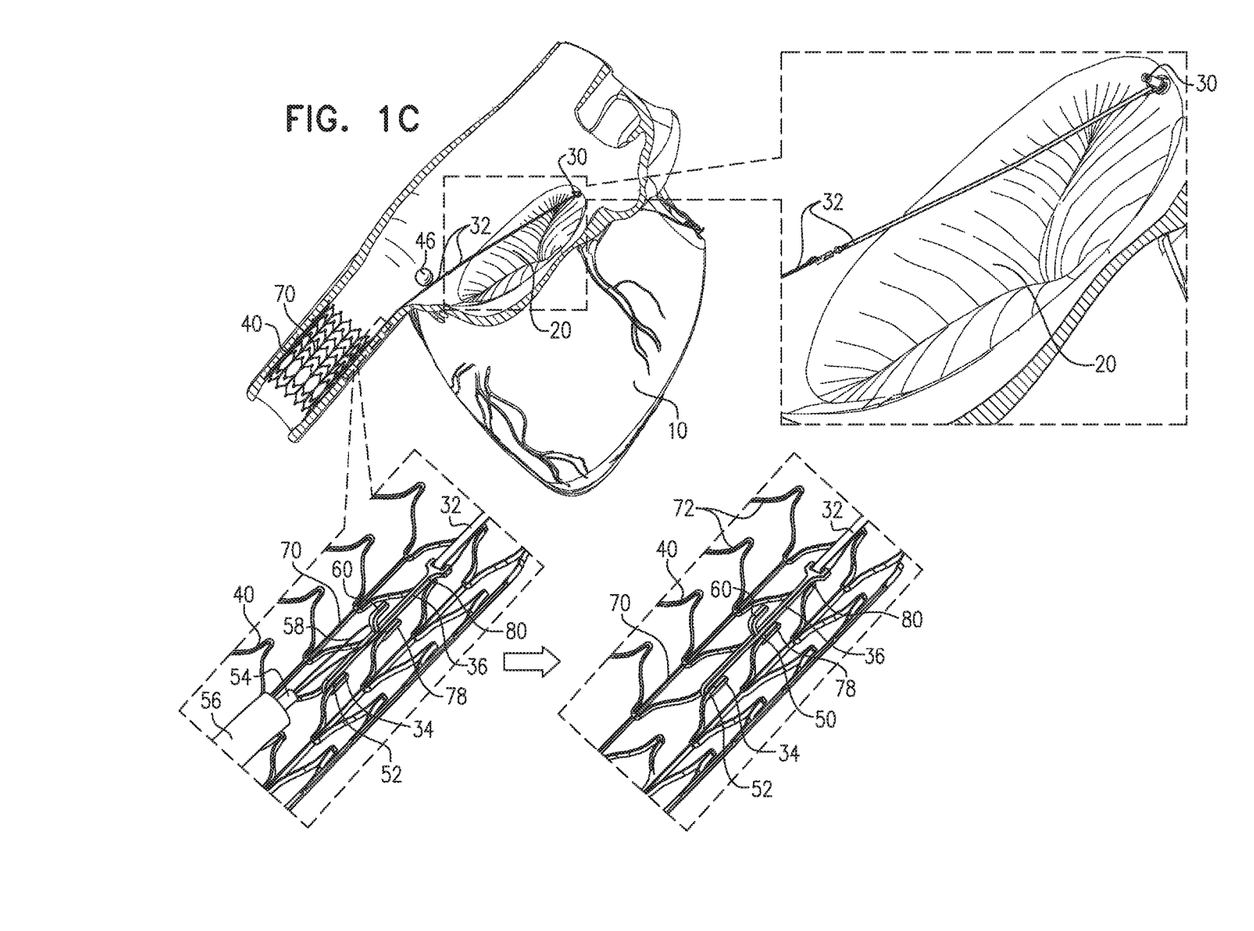
Figure 2A:
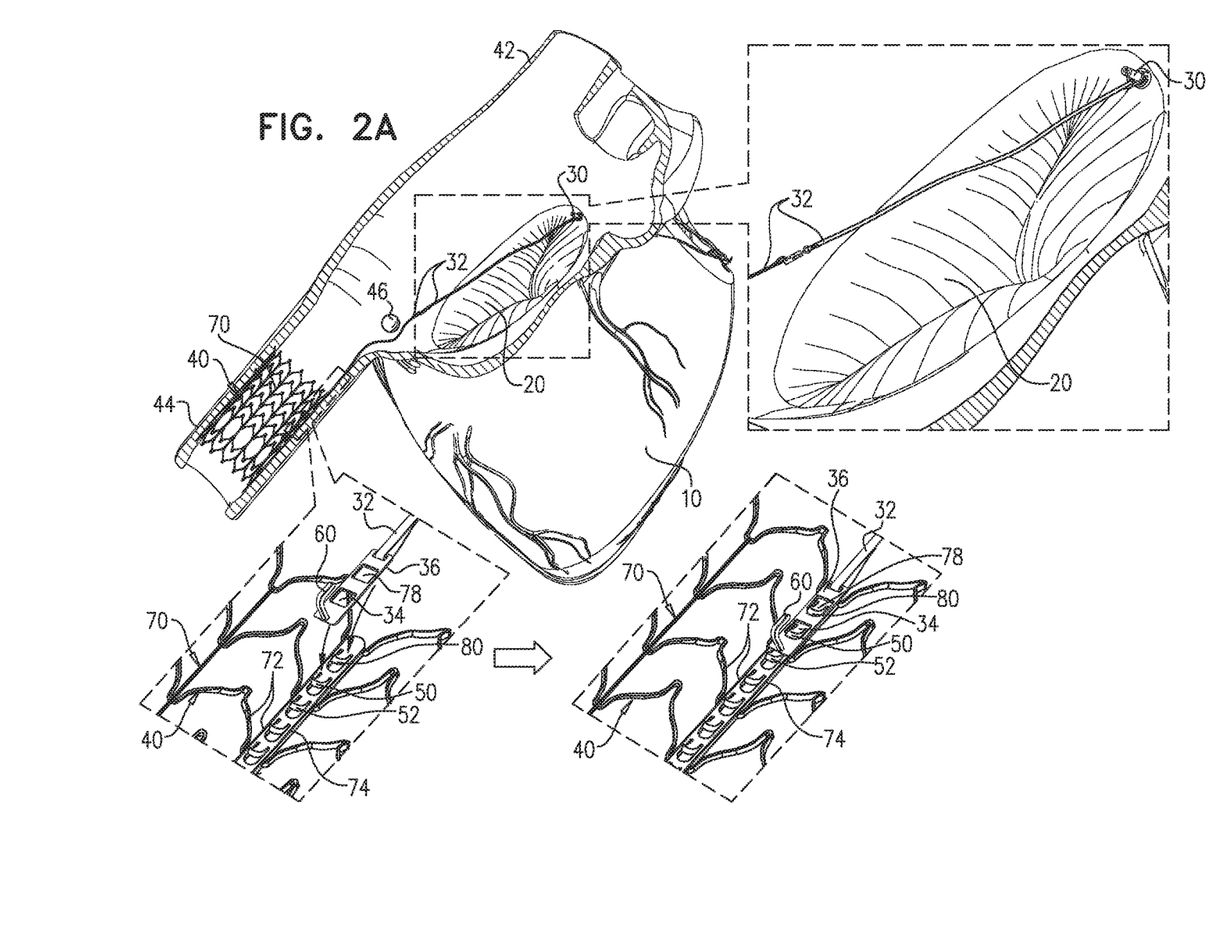
FIGS. 2A-C are schematic illustrations of a method of treating a heart of a patient, in accordance with an application of the present invention.
Figure 2B:
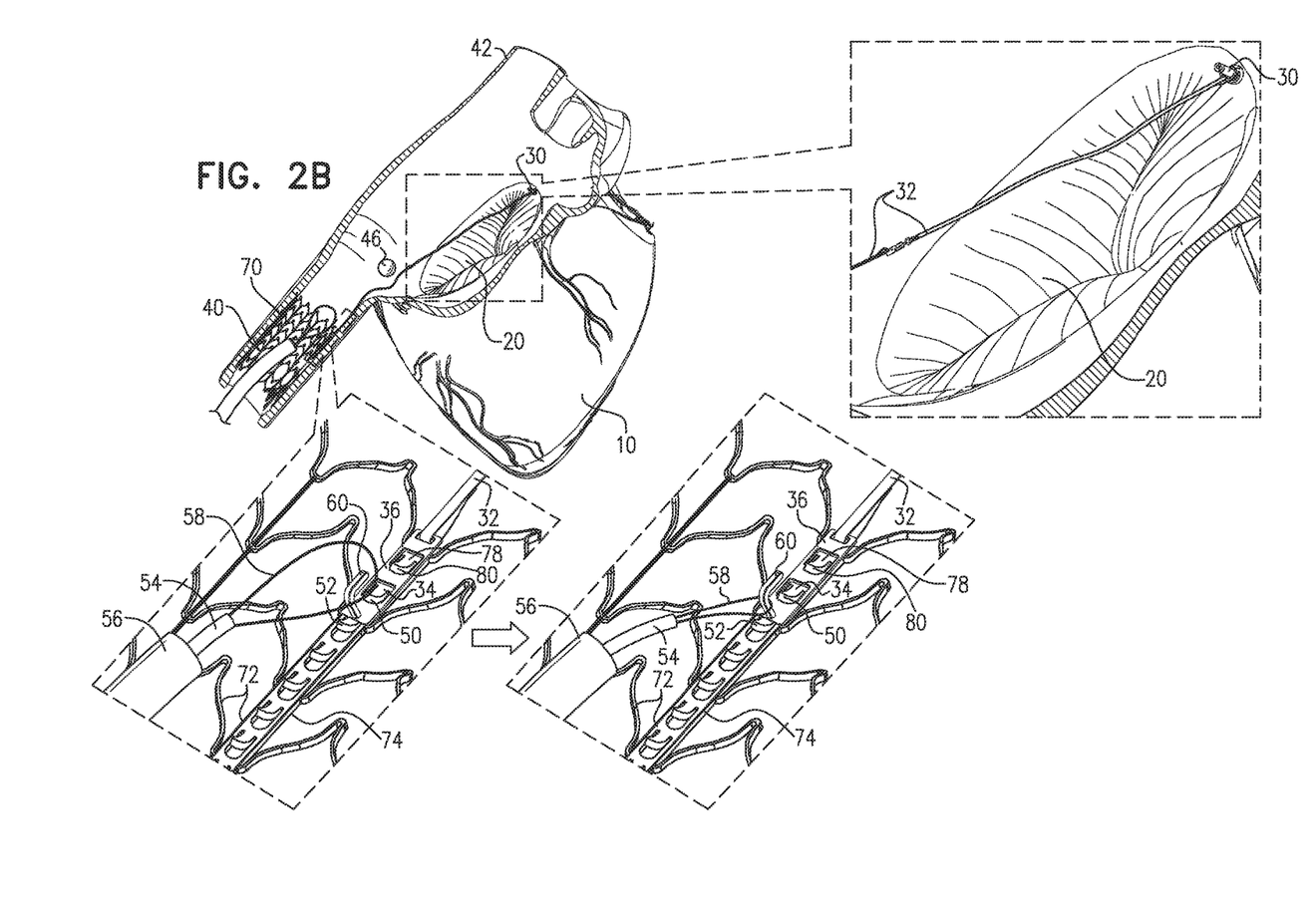
Figure 2C:
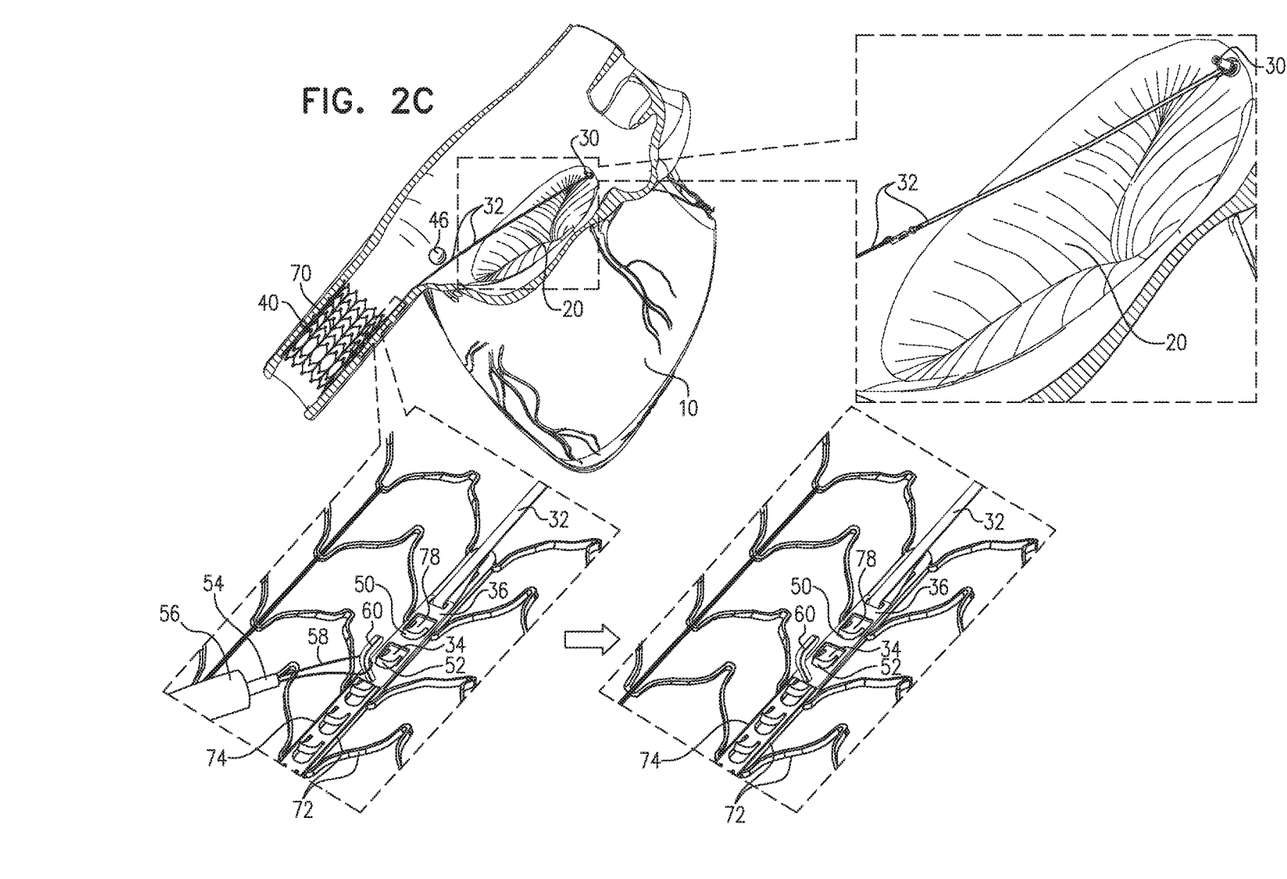

As shown in FIGS. 1A and 2A, during a first stage of an implantation procedure, a first tissue anchor 30 is implanted in cardiac tissue of the patient, such as in the vicinity of tricuspid valve 20. First tissue anchor 30 is attached to one or more tethers 32 that are fixed to a coupling element 34, such as a hook, as shown in FIGS. 1A-C, or an opening, as shown in FIGS. 2A-C. Optionally, coupling element 34 comprises a loop, which is shaped so as to define the opening (configuration not shown). Optionally, a coupling support structure 36 is provided, which comprises coupling element 34 and attaches coupling element 34 to the one or more tethers 32. A second tissue anchor 40 is implanted in the patient, either before or after implanting first tissue anchor 30, such as in a superior vena cava (SVC) 42, an inferior vena cava (IVC) 44 (as shown), and a coronary sinus 46. Typically, first and second tissue anchors 30 and 40 are implanted in a transcatheter procedure (typically endovascularly, such as percutaneously), via a catheter, such as described in the applications incorporated hereinbelow by reference. Optionally, the one or more tethers 32 comprise two tethers 32 that are coupled together in situ during the first stage of the implantation procedure, such as using techniques described in one or more of the applications incorporated by reference hereinbelow.

Also as shown in FIGS. 1A and 2A, coupling element 34 is coupled to a first coupling site 50 of second tissue anchor 40, thereby coupling first tissue anchor 30 to second tissue anchor 40 via the one or more tethers 32. Coupling element 34 may be coupled to first coupling site 50 either after or before implanting first and second tissue anchors 30 and 40, or after implanting first tissue anchor 30 and before implanting second tissue anchor 40. For some applications, at this first stage of the implantation procedure, the one or more tethers 32 are slack, i.e., do not apply tension between first and second tissue anchors 30 and 40.

As shown in FIGS. 1B-C and 2B-C, thereafter, during a second stage of the implantation procedure, typically after allowing at least 24 hours (e.g., at least one week, such as at least one month) for tissue growth (e.g., fibrous and/or endothelial tissue growth) on first tissue anchor 30 to strengthen anchoring of first tissue anchor 30 in the cardiac tissue, tension is increased between first and second tissue anchors 30 and 40 by decoupling coupling element 34 from first coupling site 50 and coupling coupling element 34 to a second coupling site 52 of second tissue anchor 40 (different from first coupling site 50). For some applications, the tension is increased within two months after implanting first tissue anchor 30. Typically, second coupling site 52 is farther from first tissue anchor 30 than first coupling site 50 is from first tissue anchor 30. Typically, application of the tension remodels tricuspid valve 20, by drawing two or three of the leaflets together to enhance coaptation. The procedure may optionally include subsequent stages (e.g., a third stage) after the second stage (e.g., at least 24 hours after the second stage), in which tension is further increased by decoupling coupling element from its current coupling site (e.g., coupling site 50) and coupling coupling element 34 to yet another coupling site (e.g., a third coupling site).

Typically, in order to decouple coupling element 34 from first coupling site 50, during the second stage of the implantation procedure a tool 54 is introduced through the vasculature via a catheter 56, and used to recapture coupling element 34. For example, tool 54 may comprise a lasso 58, which is used to engage a hook 60 of coupling element 34. The hook may extend radially inward into a lumen of second tissue anchor 40 in order to facilitate engagement by tool 54 (e.g., lasso 58) when tool 54 has been introduced into the lumen of second tissue anchor 40.

For some applications, as shown in the figures, second tissue anchor 40 comprises a stent 70 that comprises a plurality of struts 72, which define first and second coupling sites 50 and 52. For some applications, such as shown in FIGS. 1A-C and 2A-C, first and second coupling sites 50 and 52 extend radially inward (i.e., toward a central longitudinal axis of stent 70) to facilitate the coupling of coupling element 34 to first and second coupling sites 50 and 52 from within stent 70. For some of these applications, such as shown in FIGS. 1A-C, one or more of struts 72 extend radially inward at first and second couplings sites 50 and 52 to facilitate the coupling of coupling element 34 to first and second coupling sites 50 and 52 from within stent 70. For others of these applications, such as shown in FIGS. 2A-C, second tissue anchor 40 comprises hooks (which are optionally shaped as tabs, as shown in FIGS. 2A-C) at first and second coupling sites 50 and 52, respectively; the hooks, and thus first and second coupling sites 50 and 52, extend radially inward (optionally, one or more of struts 72 (e.g., axially-oriented strut 74, described immediately below) also extend radially inward).

For some applications, at least one 74 of struts 72 is oriented axially along the stent, and axially-oriented strut 74 defines first and second coupling sites 50 and 52. Optionally, axially-oriented strut 74 is wider than others of struts 72 so as to serve as a backbone for the stent. (Although not illustrated, this backbone may also be provided for the configuration shown in FIGS. 1A-C.)

For some applications, first tissue anchor 30 comprises a helical tissue-anchoring element. For some applications, fibrous glue is applied to the tissue-coupling element to help secure the anchor in place and minimize detachment. Optionally, tissue-growth-enhancing coating is also applied to the tissue-coupling element.

For some applications, coupling element 34 is a first coupling element 34, and the one or more tethers 32 are additionally fixed to a second coupling element 78, such as a hook, as shown in FIGS. 1A-C, or an opening, as shown in FIGS. 2A-C (or to more than two coupling elements, such as shown in FIGS. 2A-C); for example, coupling support structure 36, if provided, may comprise second coupling element 78 in addition to first coupling element 34. For these applications, coupling coupling element 34 to first coupling site 50 comprises coupling one or more of first and second coupling elements 34 and 78 to a plurality of first coupling sites 50. Providing a plurality of coupling elements provides redundancy; in case one of the coupling elements does not catch on second tissue anchor 40, another of the coupling elements may catch (or both may catch, as shown in the figures).

For some applications, first and second coupling elements 34 and 78 are arranged along coupling support structure 36, optionally at a distance apart that is the same as a distance between first and second coupling sites 50 and 52, such that when first coupling element 34 is repositioned from first coupling site 50 to second coupling site, as described hereinabove with reference to FIGS. 1B-C and 2B-C, second coupling element 78 is repositioned from a third coupling site 80 to first coupling site 50, i.e., takes the coupling site vacated by first coupling element 34.

For some applications, coupling element 34, first coupling site 50, and/or second coupling site 52 are coated with a tissue-growth-inhibiting coating (e.g., silicone). Such coating may facilitate the decoupling of coupling element 34 from first coupling site 50 and/or the coupling of coupling element 34 to second coupling site 52, as described hereinabove with reference to FIGS. 1B-C and 2B-C.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Pat. No. 8,475,525 to Maisano et al.;
U.S. Pat. No. 8,961,596 to Maisano et al.;
U.S. Pat. No. 8,961,594 to Maisano et al.;
PCT Publication WO 2011/089601;
U.S. Pat. No. 9,241,702 to Maisano et al.;
PCT Publication WO 2013/011502;
U.S. Provisional Application 61/750,427, filed Jan. 9, 2013;
U.S. Provisional Application 61/783,224, filed Mar. 14, 2013;
PCT Publication WO 2013/179295;
U.S. Provisional Application 61/897,491, filed Oct. 30, 2013;
U.S. Provisional Application 61/897,509, filed Oct. 30, 2013;
U.S. Pat. No. 9,307,980 to Gilmore et al.;
PCT Publication WO 2014/108903;
PCT Publication WO 2014/141239;
U.S. Provisional Application 62/014,397, filed Jun. 19, 2014;
PCT Publication WO 2015/063580;
US Patent Application Publication 2015/0119936;
U.S. Provisional Application 62/086,269, filed Dec. 2, 2014;
U.S. Provisional Application 62/131,636, filed Mar. 11, 2015;
U.S. Provisional Application 62/167,660, filed May 28, 2015;
PCT Publication WO 2015/193728;
PCT Publication WO 2016/087934;
US Patent Application Publication 2016/0242762;
PCT Publication WO 2016/189391;
US Patent Application Publication 2016/0262741; and
U.S. Provisional Application 62/376,685, filed Aug. 18, 2016.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of treating a heart of a patient, comprising:
   implanting a first tissue anchor in cardiac tissue of the patient, the first tissue anchor attached to one or more tethers that are fixed to a coupling element;
   implanting a second tissue anchor in the patient;
   coupling the coupling element to a first coupling site of the second tissue anchor, thereby coupling the first tissue anchor to the second tissue anchor via the one or more tethers; and
   thereafter, after allowing at least 24 hours for tissue growth on the first tissue anchor to strengthen anchoring of the first tissue anchor in the cardiac tissue, increasing tension between the first and the second tissue anchors by decoupling the coupling element from the first coupling site and coupling the coupling element to a second coupling site of the second tissue anchor,
   wherein a tissue-growth-inhibiting coating coats (a) the coupling element, (b) the first and the second coupling sites, or (c) the coupling element and the first and the second coupling sites.

2. The method according to claim 1, wherein the one or more tethers are slack before increasing the tension.

3. The method according to claim 1, wherein the coupling element comprises a hook.

4. The method according to claim 1, wherein the coupling element is shaped so as to define an opening, and wherein coupling the coupling element to the first coupling site comprises coupling the opening to the first coupling site.

5. The method according to claim 1, wherein the second tissue anchor comprises a stent that comprises a plurality of struts, which define the first and the second coupling sites.

6. The method according to claim 5, wherein the first and the second coupling sites extend radially inward to facilitate the coupling of the coupling element to the first and the second coupling sites from within the stent.

7. The method according to claim 6, wherein one or more of the struts extend radially inward at the first and the second couplings sites to facilitate the coupling of the coupling element to the first and the second coupling sites from within the stent.

8. The method according to claim 6, wherein the second tissue anchor comprises hooks at the first and the second coupling sites, respectively.

9. The method according to claim 5, wherein at least one of the struts is oriented axially along the stent, and the axially-oriented strut defines the first and the second coupling sites.

10. The method according to claim 9, wherein the first and the second coupling sites extend radially inward to facilitate the coupling of the coupling element to the first and the second coupling sites from within the stent.

11. The method according to claim 1, wherein increasing the tension comprises increasing the tension after allowing at least one week for tissue growth on the first tissue anchor.

12. The method according to claim 1, wherein increasing the tension comprises increasing the tension within two months after implanting the first tissue anchor.

13. The method according to claim 1, wherein the coupling element is a first coupling element, and the one or more tethers are additionally fixed to a second coupling element, and wherein coupling the coupling element to the first coupling site comprises coupling one or more of the first and the second coupling elements to a plurality of first coupling sites.

14. The method according to claim 1, wherein coupling the coupling element to the first coupling site comprises coupling the coupling element to the first coupling site after implanting the first and the second tissue anchors.

15. The method according to claim 1, wherein coupling the coupling element to the first coupling site comprises coupling the coupling element to the first coupling site before implanting the first and the second tissue anchors.

16. The method according to claim 1, wherein coupling the coupling element to the first coupling site comprises coupling the coupling element to the first coupling site after implanting the first tissue anchor and before implanting the second tissue anchor.

17. The method according to claim 1, wherein the coupling element is coated with the tissue-growth-inhibiting coating.

18. The method according to claim 1, wherein the first and the second coupling sites are coated with the tissue-growth-inhibiting coating.

19. The method according to claim 1, wherein the first tissue anchor comprises a helical tissue-anchoring element.

20. The method according to claim 1, wherein implanting the first tissue anchor comprises implanting the first tissue anchor in the vicinity of the tricuspid valve of the patient.

21. The method according to claim 1, wherein implanting the second tissue anchor comprises implanting the second tissue anchor in a blood vessel selected from the group consisting of: a superior vena cava (SVC), an inferior vena cava (IVC), and a coronary sinus.

22. The method according to claim 1, wherein the coupling element and the first and the second coupling sites are coated with the tissue-growth-inhibiting coating.

23. A method of treating a heart of a patient, comprising:
   implanting a first tissue anchor in cardiac tissue of the patient, the first tissue anchor attached to one or more tethers that are fixed to a coupling element;
   implanting a second tissue anchor in the patient;
   coupling the coupling element to a first coupling site of the second tissue anchor, thereby coupling the first tissue anchor to the second tissue anchor via the one or more tethers; and
   thereafter, after allowing at least 24 hours for tissue growth on the first tissue anchor to strengthen anchoring of the first tissue anchor in the cardiac tissue, increasing tension between the first and the second tissue anchors by decoupling the coupling element from the first coupling site and coupling the coupling element to a second coupling site of the second tissue anchor,
   wherein the second tissue anchor comprises a stent that comprises a plurality of struts, which define the first and the second coupling sites,
   wherein at least one of the struts is oriented axially along the stent, and the axially-oriented strut defines the first and the second coupling sites, and
   wherein the axially-oriented strut is wider than others of the struts so as to serve as a backbone for the stent.

* * * * *